United States Patent
Grass et al.

(10) Patent No.: US 8,022,244 B2
(45) Date of Patent: Sep. 20, 2011

(54) METHOD FOR PRODUCING BENZOIC ACID ESTERS

(75) Inventors: Michael Grass, Haltern am See (DE); Dietmar Gubisch, Marl (DE); Michael Woelk-Faehrmann, Marl (DE)

(73) Assignee: EVONIK OXENO GmbH, Marl (DE)

( * ) Notice: Subject to any disclaimer, the term of this patent is extended or adjusted under 35 U.S.C. 154(b) by 0 days.

(21) Appl. No.: 12/140,316

(22) Filed: Jun. 17, 2008

(65) Prior Publication Data

US 2008/0245996 A1    Oct. 9, 2008

Related U.S. Application Data

(62) Division of application No. 10/575,100, filed as application No. PCT/EP2004/051854 on Aug. 20, 2004, now abandoned.

(30) Foreign Application Priority Data

Oct. 10, 2003 (DE) ................................. 103 47 863

(51) Int. Cl.
*C07C 69/78* (2006.01)
(52) U.S. Cl. ..................................... 560/103
(58) Field of Classification Search .................. None
See application file for complete search history.

(56) References Cited

U.S. PATENT DOCUMENTS

| | | | | |
|---|---|---|---|---|
| 3,053,883 A | * | 9/1962 | Fred et al. ...................... 560/99 |
| 3,933,630 A | * | 1/1976 | Helgorsky et al. ............ 210/639 |
| 5,236,987 A | * | 8/1993 | Arendt ........................... 524/287 |
| 5,898,077 A | | 4/1999 | Takahara et al. |
| 6,235,924 B1 | * | 5/2001 | McConnell et al. .......... 560/103 |
| 6,916,950 B2 | | 7/2005 | Gubisch et al. |
| 2004/0015007 A1 | * | 1/2004 | Grass et al. .................... 560/103 |
| 2004/0138358 A1 | | 7/2004 | Koch et al. |
| 2004/0260113 A1 | | 12/2004 | Bueschken et al. |
| 2005/0038285 A1 | | 2/2005 | Maschmeyer et al. |
| 2005/0049341 A1 | | 3/2005 | Grass et al. |
| 2005/0101800 A1 | | 5/2005 | Bueschken et al. |
| 2006/0167151 A1 | | 7/2006 | Grass et al. |
| 2007/0060768 A1 | | 3/2007 | Grass et al. |

* cited by examiner

*Primary Examiner* — Daniel Sullivan
*Assistant Examiner* — Yevegeny Valenrod
(74) *Attorney, Agent, or Firm* — Oblon, Spivak, McClelland, Maier & Neustadt, L.L.P.

(57) ABSTRACT

A process for preparing benzoic esters whose alkoxy groups have from 7 to 13 carbon atoms by reacting benzoic acid with at least one alcohol having from 7 to 13 carbon atoms, the water of reaction formed being removed during the esterification reaction by distillation, and the alcohol not converted in the esterification reaction being removed after the esterification reaction, in which the reaction takes place in the presence of a tin(II) compound as catalyst and, without treatment with a base, the catalyst and/or its derivatives is/are separated off by filtering or by centrifuging from the reaction mixture which remains after the unconverted alcohol has been separated off.

21 Claims, No Drawings

METHOD FOR PRODUCING BENZOIC ACID ESTERS

CROSS-REFERENCE TO RELATED APPLICATIONS

The present application is a divisional of U.S. patent application 10/575,100, filed on Apr. 10, 2006, which is a 35 U.S.C. §371 National Stage patent application of International patent application PCT/EP04/051854, filed on Aug. 20, 2004, which claims priority to German patent application DE 10347863.9, filed on Oct. 10, 2003.

The present invention relates to a process for preparing benzoic esters from benzoic acid and alcohols having 7 to 13 carbon atoms.

Benzoic esters whose alkoxy groups have 7 to 13 carbon atoms are used as film-forming auxiliaries in compositions such as emulsion paints, mortars, renders, adhesives, and varnishes. Additionally they can be used as plasticizers and/or viscosity reducers in flexible (unplasticized) PVC applications, especially in plastisols.

The preparation of carboxylic esters by reaction of carboxylic acids with alcohols is known. This reaction can be carried out autocatalytically or catalytically, by means of Bronsted or Lewis acids, for example. Irrespective of the type of catalysis selected, a temperature-dependent equilibrium is always developed between the reactants (carboxylic acid and alcohol) and the products (ester and water). In order to shift the equilibrium in favor of the ester, many esterifications use an azeotrope former, with whose aid the water of reaction is removed from the reaction mixture. If one of the reactants (alcohols or carboxylic acid) has a lower boiling point than the ester formed and forms a miscibility gap with water, that reactant can be used as an azeotrope former and, following removal of the water, can be recycled to the batch. In the case of esterification of carboxylic acids the alcohol employed is frequently used as an azeotrope former.

Many end-use applications require the ester prepared by esterifying a carboxylic acid to possess a low acid number—in other words, the conversion of the carboxylic acid ought to be virtually quantitative. Otherwise the yield is lessened and the acid has to be separated off, by neutralization for example. This is costly and inconvenient and can lead to by-products, which require disposal. To maximize conversion of the carboxylic acid, esterifications are generally carried out with an excess of alcohol.

Esterification catalysts used can be acids, such as sulfuric acid or p-toluenesulfonic acid, or metals and compounds thereof. Suitable examples include tin, titanium, and zirconium, which can be used as finely divided metals or, advantageously, in the form of their salts, oxides or soluble organic compounds. In contrast to protic acids, the metal catalysts are high-temperature catalysts, achieving their full activity only at temperatures above 180° C. In the art, however, they are used preferentially on account of the fact that, in comparison to proton catalysis, the level of by-products they form, such as olefins of the alcohol employed, for example, is lower. Exemplary representatives of metal catalysts are titanic esters such as tetraisopropyl orthotitanate or tetrabutyl orthotitanate, and zirconium esters such as tetrabutyl zirconate.

After the esterification has taken place, the excess reactant alcohol, residues of acid, the catalyst and/or its derivatives, and also other by-products, must be separated from the desired carboxylic ester. The economics of an esterification process are good only when both the technical complexity and the time consumed for physical separation are low.

The esterification of carboxylic acids with tin compounds is described in patents GB 2 098 211, EP 0 036 712, and EP 0 037 172. In those cases, a portion of the tin compounds is put onto a metal mesh, which is in contact with the reaction solution, while the other portion of the tin compounds is in solution and/or suspension in the reaction solution.

Esterification takes place with distillative removal of the water of reaction. After the esterification, acids still present are neutralized in a second vessel, and their salts, and tin compounds, are separated off. This is accomplished by adding a solid base to the crude ester and removing the precipitated solids (base, salts, tin compounds) by filtration, or by extracting the crude ester with an aqueous base. With these workup methods, the result is either an aqueous phase containing organic and inorganic compounds, or a solids mixture containing organic and inorganic compounds. Disposing of these by-products occasions costs which in certain circumstances are high.

U.S. Pat. No. 6,235,924 describes a process for preparing benzoic esters by reacting benzoic acid with an alcohol in the presence of a titanium catalyst. The esterification is carried out with the water of reaction being separated off by distillation. The benzoic ester is separated off from the ester mixture by means of fractional distillation. A disadvantage of this process is the time and energy consumed for the distillation.

The object was therefore to find a process for preparing benzoic esters that does not have the disadvantages of the known processes.

Surprisingly it has been found that benzoic esters of high purity can be easily prepared by reacting benzoic acid with alcohols having 7 to 13 carbon atoms in the presence of a tin(II) compound if the esterification takes place with distillative removal of the water of reaction, the esterification is followed by removal of the excess alcohol present in the reaction mixture by means of distillation and stripping with a gas or steam, and, without treatment with a base, the resultant crude ester is filtered. The filtration allows the tin catalyst and/or its tin-containing derivatives to be separated off to an extent such that the tin content of the end product (filtrate) is well below 1 mg/kg (ppm).

The present invention accordingly provides a process for preparing benzoic esters whose alkoxy groups have from 7 to 13 carbon atoms by reacting benzoic acid with at least one alcohol having from 7 to 13 carbon atoms, the water of reaction formed being removed from the reaction mixture during the esterification reaction by distillation with the alcohol used in excess, and the alcohol not converted in the esterification reaction being removed after the esterification reaction, which is characterized in that the reaction takes place in the presence of a tin(II) compound as catalyst at a temperature of 160 to 250° C. and in that, without treatment with a base, the catalyst and/or its derivatives are removed by filtering or by centrifuging from the reaction mixture which remains after the unconverted alcohol has been separated off, virtually to completion.

Likewise provided by the present invention are compositions comprising benzoic ester(s), obtainable by the process of the invention, and also their use.

The process of the invention is notable for the following advantages:
Workup, particularly the simple removal of the catalyst by filtration, is less costly and inconvenient by comparison with known methods.
With no base being added, neither salts of neutralization nor waste waters loaded with organic and inorganic substances are obtained.

The catalyst separated off, and/or its derivative(s), can be easily worked up or disposed of.

Because no bases or other auxiliaries have to be added to the reaction mixture, time and costs are saved and additional contamination of the ester is avoided.

The process of the invention for preparing benzoic esters, compositions prepared by the process, and uses thereof is/are described below, without any intention that the invention should be restricted to these embodiments.

The process of the invention for preparing benzoic esters whose alkoxy groups have from 7 to 13 carbon atoms by reaction of benzoic acid with one or more alcohols having from 7 to 13 carbon atoms, the water of reaction formed being removed from the reaction mixture during the esterification reaction by distillation with the alcohol used in excess, and the alcohol not converted in the esterification reaction being removed after the esterification reaction, is notable for the fact that the reaction takes place in the presence of a tin(II) compound as catalyst at a temperature of 160 to 250° C. and in that, without treatment with a base, the catalyst and/or its derivatives can be separated off almost completely by filtering or by centrifuging from the reaction mixture which remains after the unconverted alcohol has been separated off, so that the tin content of the end product (the filtrate) is below 1 mg/kg (ppm), in particular well below 1 mg/kg, and preferably less than 0.1 mg/kg.

Throughout the esterification reaction and also the subsequent removal of excess alcohol and catalyst, therefore, there is no treatment with a base and no neutralization step.

In the process of the invention the benzoic acid is esterified using branched or linear aliphatic alcohols or mixtures of alcohols having 7 to 13 carbon atoms. The alcohols may be monohydric or polyhydric, but are preferably monohydric. The alcohols may be secondary or primary, linear or branched. The alcohol used may comprise a mixture of alcohols having the same or different number of carbon atoms. The alcohols can be employed as an isomerically pure compound, as a mixture of isomeric compounds, or as a mixture of isomeric or isomerically pure compounds with a different number of carbon atoms.

The alcohols used may originate from a variety of sources. Examples of suitable reactant alcohols include fatty alcohols, alcohols from the Alfol process (oligomerization of ethylene in the presence of aluminum alkyls with subsequent oxidation and hydrolysis to the corresponding primary alcohols), or alcohols or alcohol mixtures obtained by hydrogenating saturated or unsaturated aldehydes, particularly those whose synthesis includes a step of hydroformylation.

Alcohols which can be used with preference in the process of the invention are, for example, heptanols, 1-octanol, 2-octanol, 2-ethylhexanol, nonanols, decyl alcohols and/or tridecanols. Particularly preferred reactant alcohols are mixtures of isomeric octanols, decanols, especially 2-propylheptanol, nonanols or tridecanols, the latter obtainable from the corresponding butene oligomers, especially oligomers of linear butenes, by hydroformylation and subsequent hydrogenation. The butene oligomers can be prepared in principle by three methods. Acid-catalyzed oligomerization, for which, for example, zeolites or phosphoric acid on supports are used industrially, yields the oligomers with the greatest branching. Using linear butenes results in, for example, a $C_8$ fraction composed substantially of dimethylhexenes (WO 92/13818). A method which is likewise implemented worldwide is that of oligomerization with soluble Ni complexes, known as the DIMERSOL process (B. Cornils, W. A. Herrmann, Applied Homogeneous Catalysis with Organometallic Compounds, pages 261-3, Verlag Chemie 1996). The oligomerization can also be implemented over fixed-bed nickel catalysts, as described for the OCTOL process, for example (Hydrocarbon Process., Int. Ed. (1986) 65 (2. Sect. 1), pages 31-3).

Especially preferred reactants for the esterification of the invention are mixtures of isomeric nonanols or mixtures of isomeric tridecanols, prepared by oligomerizing linear butenes to $C_8$ olefins and $C_{12}$ olefins by the Octol process, with subsequent hydroformylation and hydrogenation. Likewise of preferential suitability as a reactant are decyl alcohol mixtures of which more than 50% by mass comprises 2-propylheptanol. These mixtures are prepared in general by hydroformylation of butenes, hydrogenation to the corresponding pentanals, aldolization of the pentanals to the corresponding decenals, and final hydrogenation to the decanols.

The catalyst used in the process of the invention comprises one or more divalent tin compounds or else tin compounds and/or elemental tin able to react with the reactants to form divalent tin compounds. As the catalyst it is possible to make use, for example, of tin, tin(II) chloride, tin(II) sulfate, tin(II) alkoxides or tin(II) salts of organic acids, especially of monocarboxylic and dicarboxylic acids. Preferred tin catalysts are tin(II) oxalate and/or tin(II) benzoate.

It has proven advantageous if a molar ratio of tin to benzoic acid of preferably $10^{-5}$ to $10^{-3}$:1, more preferably of $10^{-4}$ to $10^{-3}$:1, is set at the beginning of the reaction.

The esterification is carried out in a reaction vessel (reactor) inl which the reaction batch can be mixed intensively with the aid of a stirrer or circulation pump. The reactants and the catalyst can be introduced into the reactor simultaneously or in succession. Where the benzoic acid is in solid form at the introduction temperature, it can be advantageous to introduce the alcohol or alcohol mixture to start with. The benzoic acid can be fed in as a powder, granules, crystallizate or melt. It is likewise possible for the benzoic acid to be fed into the reactor in solution in a solvent, preferably in an alcohol, and more preferably in an alcohol likewise used as a reactant. In order to shorten the batch time it is advantageous to commence heating during the introduction procedure. The catalyst can be introduced into the reactor in a pure form, as a suspension or as a solution, preferably in alcohol or alcohol mixture employed, at the start or not until after the reaction temperature has been attained. The volume of catalyst to be employed can be added all at once or in two or more portions.

The alcohol to be converted, which also serves as an azeotrope former, is employed in a stoichiometric excess, with an excess of preferably 5% to 50%, more preferably 10% to 30%, of the amount required by stoichiometry.

In the process of the invention the reaction temperatures are situated in the range from 160° C. to 250° C., preferably from 180° C. to 230° C., more preferably from 190° C. to 210° C. The optimum temperatures depend on the reactant alcohol(s), the progress of the reaction, the type of catalyst, and the catalyst concentration. For each specific case they can be determined readily by means of tests. Higher temperatures raise the reaction rates and favor side reactions, such as elimination of water from alcohols or formation of colored by-products, for example. For the removal of the water of reaction it is necessary for the alcohol to be removable from the reaction mixture by distillation. The desired temperature or temperature range can be set via the pressure in the reaction vessel (slight overpressure-atmospheric pressure-underpressure).

In the case of the esterification of benzoic acid with a mixture of isomeric nonanols, for example, it is particularly preferred to operate in a temperature range from 190° C. to 210° C. in the pressure range from 1 bar to 100 mbar.

The water of reaction formed during the esterification reaction is removed in the course of the ongoing esterification reaction by means of distillation, in particular an azeotropic distillation. This measure removes not only the water of reaction but also a portion of the alcohol. It is possible to replace some or all of the volume of liquid removed by the azeotropic distillation, by separating the liquid separated off into an organic phase, which besides the alcohol may also contain benzoic ester(s), and into an aqueous phase, and recycling the organic phase into the esterification reaction. As an option, fresh alcohol can be added to the separated-off organic phase which is recycled into the reaction.

The liquid removed from the reaction mixture by distillation in the course of the removal of the water of reaction is preferably replaced by a corresponding volume of liquid which is added again to the reaction mixture. The volume of liquid to be recycled into the reaction may be composed in part or in whole of the reactant alcohol or reactant alcohol mixture. The volume of liquid removed from the reaction mixture during the esterification by (azeotropic) distillation can be at least partly made up, for example, by separation of the liquid separated off into an aqueous phase and an organic phase and recycling of the organic phase into the esterification reaction. It is also possible for the reaction mixture to be made up in whole or in part by the volume of liquid removed from the reaction mixture during the esterification by (azeotropic) distillation, by separation of the liquid separated off into an aqueous phase and an organic phase and recycling of the organic phase, additionally admixed with fresh alcohol, into the esterification reaction. A further possibility is to replace some or all of the volume of liquid removed from the reaction mixture by (azeotropic) distillation by fresh alcohol, i.e., alcohol standing ready in a stock vessel.

The alcohol/water mixture removed distillatively from the reaction mixture in the course of the reaction, as an azeotrope or with a virtually azeotropic composition, may where appropriate additionally comprise benzoic ester(s). The vapors obtained leave the reaction vessel, via, for example, a short column (internals or structured packings; 1 to 5, preferably 1 to 3, theoretical plates), and are condensed. In a phase separator or a coalescer, for example, the condensate can be separated into an aqueous phase and an organic phase. It can be advantageous to cool the separated-off azeotrope to far below the condensation temperature of the vapors, thereby achieving more effective phase separation. The aqueous phase is separated off and, after workup where appropriate, can be discarded or else used as stripping water for the aftertreatment of the ester.

The organic phase obtained after separation of the azeotropic distillate can be recycled partly or wholly into the reaction vessel. In the art a level-controlled fill level monitoring system in the reaction has been found appropriate for supplying the alcohol; in such a system, when the amount of alcohol or alcohol mixture obtained through distillation is insufficient, the addition of fresh alcohol is advantageous.

For supplying the organic phase to the esterification reaction there are a variety of possibilities. For example, the organic phase can be fed to the column as a return flow. Another possibility is to pump the organic phase, after heating where appropriate, into the liquid reaction mixture. As a result of the removal of the water of reaction, there is a fall in the reaction volume in the apparatus. It is advantageous, however, as described in DE 100 43 545.9 (shorter reaction time), to feed in additionally, during the reaction, an amount of alcohol corresponding to the volume of the removed distillate (water and, where appropriate, alcohol), so that the fill level in the reaction vessel remains constant. The increase in the excess of alcohol shifts the equilibrium in favor of the benzoic ester(s).

After the end of the reaction the reaction mixture comprises benzoic ester(s), excess alcohol(s), and catalyst and derivative(s) thereof, and also any low-boiling and/or high-boiling by-products. Preferably the reaction is carried out such that there is virtually no free benzoic acid left in the reaction mixture—that is, the benzoic acid has undergone virtually complete esterification. A measure used for this purpose is the acid number to DIN EN ISO 2114. The product of the process of the invention has an acid number of preferably <0.1 mg KOH/g, more preferably <0.07 mg KOH/g, very preferably <0.04 mg KOH/g.

The unconverted alcohol can be removed by stripping, distilling or steam-distillation or by a combination of two or more of these methods. The unconverted alcohol is preferably separated off after the esterification reaction by vacuum distillation and subsequent stripping with steam or nitrogen.

The removal of the excess alcohol can be carried out, for example, initially by vacuum distillation, optionally without further supply of energy, selectively down to an alcohol concentration below 10%, preferably below 5%, more preferably below 3%, very preferably below 1% in the reaction mixture. The distillation conditions for this are, in terms of temperature, preferably from 160 to 250° C., more preferably from 180 to 230° C.; the pressure is preferably from 5 mbar to 1 bar. When preparing isononyl benzoate the vacuum distillation is carried out, for example, at a preferred distillation temperature of 180 to 210° C. and a preferred distillation pressure of 10 to 320 mbar.

After the vacuum distillation the remaining alcohol and any residual low boilers present can be removed by stripping with an inert gas, such as nitrogen, for example, or steam in the temperature range from 130 to 240° C. Stripping takes place preferably with steam in the temperature range from 170 to 220° C. under a pressure of 20 to 500 mbar, more preferably from 20 to 150 mbar. Both for stripping and for vacuum distillation, pressure and temperature are to be selected in each case such that the ester remains in the liquid phase in the bottom of the column, while the alcohol or alcohols, and any low boilers present, are separated off in gas form.

In one particular embodiment of the process of the invention it is also possible to dispense with the vacuum distillation and to remove the entire excess of alcohol and low-boiling by-products by stripping alone. Stripping can be carried out batchwise, in the reaction vessel for example. Stripping can also be carried out, optionally, continuously, in a packed column for example. The amount of residual alcohol and low-boiling by-products can be lowered in this way (by stripping alone) to below 500 ppm, preferably below 300 ppm, more preferably below 200 ppm.

A feature of the process of the invention is that no base is added before, during or after the removal of alcohol. After the alcohol has been removed, the ester which remains is centrifuged or filtered, optionally with the addition of a filter aid, in order to remove the catalyst. The filter medium used may comprise customary filters, such as paper filters, filter cloths, polymeric or ceramic membranes, metal screens, composite membranes and/or the filter cake itself. For centrifuging it is possible in principle to use all commercially customary centrifuges. The catalyst is separated off preferably at a temperature less than 160° C., preferably in the temperature range from 20 to 150° C., the temperature of the mixture being more preferably from 80 to 130° C. With particular preference the catalyst and/or derivative(s) thereof is/are separated from the reaction mixture, after the alcohol has been separated off and without base treatment, by filtration at temperatures between 100 and 130° C. Even at these relatively high temperatures, adequate removal of the catalyst by filtration is possible. Only by means of the process of the invention has it been possible to dispense with lengthy cooling to ambient temperature prior to catalyst removal.

The product which is obtained after the catalyst has been separated off (benzoic ester or mixture of two or more benzoic esters) can be obtained with a high purity. Depending on the purity of the reactants, the benzoic ester purity is typically more than 99%, preferably more than 99.5%, more preferably more than 99.7%. The amount of tin compounds, calculated as metallic tin, is below 1 mg/kg (ppm), preferably below 0.1 mg/kg. The acid number of the product in accordance with DIN EN ISO 2114 is preferably below 0.1 my KOH/g.

After the catalyst has been separated off by filtration, the reaction mixture is obtainable with the purity described above. Further purification for the purpose of separating off any relatively high-boiling impurities that may be present, by means of fractional vacuum distillation, is indeed an option, but is generally unnecessary.

The process of the invention can be carried Dut in one container or in a plurality of vessels in series, in each case preferably stirred reactors. Thus, for example, the esterification and the workup can take place in different vessels.

The alcohol separated off in the course of working up, which where appropriate may contain benzoic ester(s) and/or by-products, may be used for the subsequent batch, following removal of a portion where appropriate.

By means of the process of the invention it is possible to obtain compositions which comprise benzoic ester(s), and which in particular may comprise isononyl benzoate. These compositions can be used in paints, varnishes, adhesives or components of adhesive or as plasticizers for plastics, preferably PVC, more preferably in PVC plastisols.

The examples which follow are intended to elucidate the invention in more detail without restricting the scope of protection as provided by the description and the claims.

EXAMPLE 1

Preparation of Isononyl Benzoate with Tin Oxalate Catalyst (Inventive)

The esterification of benzoic acid with isononanol was carried out in a heatable 4-liter three-neck flask equipped with a stirrer, internal thermometer, dip tube with sampling point, and water separator with top-mounted condenser. The apparatus was capable of evacuation via the water separator with condenser. The water separator was filled with isononanol. The flask was charged with 915 g of benzoic acid (DSM Fine Chemicals, purity >99.9%), 1296 g of isononanol (OXENO Olefinchemie GmbH), and 0.55 g of tin oxalate (Aldrich), and this initial charge was heated to 210° C. with stirring. After it had reached 210° C., the heating output was reduced, and temperature and reflux were held constant via reduced pressure. The water obtained in the water separator was separated off, while the alcohol obtained ran back into the reaction flask. Where water was drained from the water separator, the amount removed was replaced by addition of pure alcohol, in order to maintain the fill level constant in the reaction flask.

The progress of the esterification was monitored at regular intervals via the acid number. Esterification was ended when the acid number was less than 0.04 mg KOH/g. The esterification time required for this, counted from the beginning of boiling, was approximately 3 hours.

For the purpose of workup, a 10-cm Multifill column with top-mounted Claisen bridge was attached in place of the water separator, and the excess alcohol was distilled off at a temperature of 180° C. and a pressure of 10 mbar.

To purify the crude ester obtained in this way as the bottom product, water was injected via the dip tube (8% by mass, based on the amount of crude ester). The temperature at this stage was kept constant at 180° C.

After the end of the steam-distillation, the ester was cooled to 100° C. under reduced pressure and filtered under reduced pressure via a suction filter with filter paper (Filtrak, moderately wide-pored, type 389) via a filter cake 1.5 cm thick, which was composed of Filterperl D14 filter aid (Perlite).

The resultant ester was colorless (APHA 19, Hazen color number, in accordance with DIN ISO 6271) and clear and had a purity of 99.96% by mass (determined by gas chromatography) and an acid number of 0.01 mg KOH/g (determined in accordance with DIN EN ISO 2114). The residual alcohol content was 74 ppm, determined by gas chromatography. The tin content was 10 ag/kg (ppb, determined by means of atomic spectrometry (ICP-OES) in accordance with DIN EN ISO 11885). The ester remained clear even after cooling to room temperature.

EXAMPLE 2

Preparation of Isononyl Benzoate with Tetrabutyl Titanate Catalyst (without Neutralization, Comparative Example)

The esterification of benzoic acid with isononanol was carried out in a heatable 4-liter three-neck flask equipped with a stirrer, internal thermometer, dip tube with sampling point, and water separator with top-mounted condenser. The apparatus was capable of evacuation via the water separator with condenser. The water separator was filled with isononanol (OXENO Olefinchemie GmbH). The flask was charged with 915 g of benzoic acid (DSM Fine Chemicals, purity >99.9%), 1296 g of isononanol and 0.55 g of tetra-n-butyl titanate (Fluka), and this initial charge was heated to 210° C. with stirring. After it had reached 210° C., the heating output was reduced, and temperature and reflux were held constant via reduced pressure. The water obtained in the water separator was separated off, while the alcohol obtained ran back into the reaction flask. Where water was drained from the water separator, the amount removed was replaced by addition of pure alcohol, in order to maintain the fill level constant in the reaction flask.

The progress of the esterification was monitored at regular intervals via the acid number. Esterification was ended when the acid number was less than 0.04 mg KOH/g. The esterification time required for this, counted from the beginning of boiling, was approximately 2.5 hours.

For the purpose of workup, a 10-cm Multifill column with top-mounted Claisen bridge was attached in place of the water separator, and the excess alcohol was distilled off at a temperature of 180° C. and a pressure of 10 mbar.

To purify the crude ester obtained in this way, water was injected via the dip tube (8% based on the amount of crude ester). The temperature at this stage was kept constant at 180° C.

After the end of the steam-distillation, the ester was cooled to 100° C. under reduced pressure and filtered under reduced pressure via a suction filter with filter paper (Filtrak, moderately wide-pored, type 389) via a filter cake 1.5 cm thick, which was composed of Filterperl D14 filter aid (Perlite).

The resultant ester was colorless (APHA 19, Hazen color number, in accordance with DIN ISO 6271) and clear and had a purity of 99.96% (determined by gas chromatography) but a significantly increased acid number of 0.12 mg KOH/g. The residual alcohol content was 197 ppm, determined by gas chromatography. The titanium content was 33 mg/kg (determined by means of atomic spectrometry (ICP-OES) in accordance with DIN EN ISO 11885). After cooling to room temperature the ester turned turbid. Only by means of additional purification steps, such as washing, draining off the wash water and drying by renewed heating, for example, was it possible to obtain a product which had an acid number of <0.05 mg KOH/g and a titanium content of <0.1 mg/kg and which remained clear even after cooling to room temperature.

EXAMPLE 3

Preparation of Isononyl Benzoate with Tetrabutyl Titanate Catalyst (with Neutralization, Comparative Example)

The esterification of benzoic acid with isononanol (OXENO Olefinchemie GmbH), was carried out in a heatable 4-liter three-neck flask equipped with a stirrer, internal thermometer, dip tube with sampling point, and water separator with top-mounted condenser. The apparatus was capable of evacuation via the water separator with condenser. The water separator was filled with isononanol. The flask was charged with 915 g of benzoic acid (DSM Fine Chemicals, purity >99.9%), 1296 g of isononanol and 0.55 g of tetra-n-butyl titanate (Fluka), and this initial charge was heated to 210° C. with stirring. After it had reached 210° C., the heating output was reduced, and temperature and reflux were held constant via reduced pressure. The water obtained in the water separator was separated off, while the alcohol obtained ran back into the reaction flask. Where water was drained from the water separator, the amount removed was replaced by addition of pure alcohol, in order to maintain the fill level constant in the reaction flask.

The progress of the esterification was monitored at regular intervals via the acid number. Esterification was ended when the acid number was less than 0.1 mg KOH/g. The esterification time required for this, counted from the beginning of boiling, was approximately 2 hours.

This was followed by cooling to 80° C. and neutralization using 6 times the stoichiometrically required amount as determined from the acid number of aqueous sodium hydroxide solution (5% by weight). After that, the mixture was stirred at this temperature for approximately another 30 minutes.

For the purpose of workup, a 10-cm Multifill column with top-mounted Claisen bridge was attached in place of the water separator, the product was heated to 180° C., and the excess alcohol was distilled off at a temperature of 180° C. and a pressure of 10 mbar.

To purify the crude ester obtained in this way, water was injected via the dip tube (8% based on the amount of crude ester). The temperature at this stage was kept constant at 180° C.

After the end of the steam-distillation, the ester was cooled to 100° C. under reduced pressure and filtered under reduced pressure via a suction filter with filter paper (Filtrak, moderately wide-pored, type 389) via a filter cake 1.5 cm thick, which was composed of Filterperl D14 filter aid (Perlite).

The resultant ester was colorless (APHA 14, Hazen color number, in accordance with DIN ISO 6271) and initially clear and had a purity of 99.98% (determined by gas chromatography) and an acid number of 0.01 mg KOH/g. The residual alcohol content was 104 ppm, determined by gas chromatography.

After cooling to room temperature, however, a precipitate was formed, necessitating further workup (filtration, for example). The titanium content determined after working up was below the detection limit of 0.1 mg/kg (determined by means of atomic spectrometry (ICP-OES) in accordance with DIN EN ISO 11885).

As is readily apparent from Examples 1 to 3, the process of the invention makes it possible in a simple way, without neutralization and without an additional workup step, to prepare a benzoic ester having a metal content of less 1 mg/kg.

EXAMPLE 4

Preparation of Isotridecyl Benzoate (Inventive)

The esterification of benzoic acid with isotridecanol was carried out in a heatable 4-liter three-neck flask equipped with a stirrer, internal thermometer, dip tube with sampling point, and water separator with top-mounted condenser. The water separator was filled with isotridecanol (OXENO Olefinchemie GmbH). The flask was charged with 732 g of benzoic acid (DSM Fine Chemicals, purity >99.9%), 1600 g of isotridecanol and 0.44 g of tin oxalate (Aldrich), and this initial charge was heated to 210° C. with stirring. After it had reached 210° C., the heating output was reduced, and temperature and reflux were held constant via addition of toluene. The water obtained in the water separator was separated off, while the alcohol/toluene mixture obtained ran back into the reaction flask. Where water was drained from the water separator, the amount removed was replaced by addition of pure alcohol. The progress of the esterification was monitored at regular intervals via the acid number.

Esterification was ended when the acid number was less than 0.04 mg KOH/g. The esterification time required for this, counted from the beginning of boiling, was 3 hours.

For the purpose of workup, a 10-cm Multifill column with top-mounted Claisen bridge was attached in place of the water separator, and the excess alcohol was distilled off at up to 210° C., 10 mbar.

To purify the crude ester obtained in this way, water was injected via the dip tube (8% based on the amount of crude ester). The temperature at this stage was kept constant at 180° C.

After the end of the steam-distillation, the ester was cooled to 100° C. under reduced pressure and filtered under reduced pressure via a suction filter with filter paper (Filtrak, moderately wide-pored, type 389) via a filter cake 1.5 cm thick, which was composed of Filterperl D14 filter aid (Perlite).

The resultant ester was clear and colorless (APHA=15, Hazen color number, in accordance with DIN ISO 6271). The purity was 99.97% (determined by gas chromatography) with a residual alcohol content of 280 ppm (determined by gas chromatography). The acid number of the ester was 0.026 mg KOH/g. The tin content is below 1 mg/kg (determined by means of atomic spectrometry (ICP-OES) in accordance with DIN EN ISO 11885).

The invention claimed is:

1. A process for producing a composition comprising a benzoate mixture of isononyl benzoate and one or more benzoic esters whose alkoxy groups have from 7 to 13 carbon atoms, wherein said process comprises:
    reacting in a reaction mixture, via an esterification reaction, benzoic acid with an alcohol comprising a mixture of isononanol and at least one alcohol having from 7 to 13 carbon atoms present, wherein the alcohol is used in stoichiometric excess, wherein the esterification reaction takes place at a reaction temperature of from 180° C. to 210° C. in the presence of a tin(II) catalyst selected from the group consisting of tin(II) chloride, tin(II) sulfate and tin(II) benzoate, and wherein the esterification reaction takes place in the presence of a solvent consisting of the alcohol;

removing from the reaction mixture by azeotropic vacuum distillation a liquid comprising water being formed during the esterification reaction, and unreacted alcohol, wherein the azeotropic vacuum distillation is carried out at a distillation temperature of from 180° C. to 210° C. and at a distillation pressure of from 10 mbar to 320 mbar;

removing from the reaction mixture after completion of the esterification reaction unreacted alcohol; and directly filtering or centrifuging off from the reaction mixture at a temperature of 100-130° C., without base treatment and without additional purification, tin(II) catalyst remaining after the removal of unreacted alcohol to produce the benzoate mixture having a tin(II) concentration of less than 1 mg/kg (ppm).

2. The process according to claim 1, wherein said removing of unreacted alcohol from the reaction mixture is carried out by distillation, stripping, or a combination thereof.

3. The process according to claim 1, wherein said filtering or centrifuging off of tin(II) catalyst from the reaction mixture is carried out at a temperature of less than 160° C.

4. The process according to claim 1, wherein said process further comprises replacing during the esterification reaction all or a portion of the volume of liquid removed from the reaction mixture with recycled alcohol.

5. The process according to claim 1, wherein said process further comprises replacing during the esterification reaction all or a portion of the volume of liquid removed from the reaction mixture with fresh alcohol.

6. The process according to claim 1, wherein said process further comprises separating the liquid removed from the reaction mixture into an aqueous phase and an organic phase and recycling the organic phase into the reaction mixture during the esterification reaction.

7. The process according to claim 1, wherein said process further comprises separating the liquid removed from the reaction mixture into an aqueous phase and an organic phase and recycling the organic phase, which is admixed with fresh alcohol, into the reaction mixture during the esterification reaction.

8. The process according to claim 1, wherein the at least one alcohol having from 7 to 13 carbon atoms is selected from linear or branched, monohydric or polyhydric, optionally isomerically pure alcohols having the same or different number of carbon atoms.

9. The process according to claim 1, wherein the at least one alcohol is selected from monohydric heptanols, octanols, nonanols, decanols, and tridecanols.

10. The process according to claim 1, wherein the monohydric octanols are selected from 1-octanol, 2-octanol and 2-ethylhexanol, and the monohydric decanol is 2-propylheptanol.

11. The process according to claim 1, wherein the alcohol is used in stoichiometric excess of 5-50%.

12. The process according to claim 1, wherein a molar ratio of tin(II) to benzoic acid is from $10^{-5}:1$ to $10^{-3}:1$ immediately prior to said reacting.

13. The process according to claim 1, wherein the benzoate mixture has a tin(II) concentration of less than 0.1 mg/kg (ppm).

14. The process according to claim 1, wherein the benzoic acid is esterified to an acid number of less than 0.1 mg KOH/g as determined in accordance with DIN EN ISO 2114.

15. The process according to claim 1, wherein the benzoic acid is esterified to an acid number of less than 0.04 mg KOH/g as determined in accordance with DIN EN ISO 2114.

16. The process according to claim 1, wherein the benzoate mixture comprises isononyl benzoate and one or more benzoic esters in a combined amount of greater than 99.5%.

17. The process according to claim 1, wherein the benzoate mixture comprises isononyl benzoate and one or more benzoic esters in a combined amount of greater than 99.7%.

18. The process according to claim 1, wherein the benzoate mixture comprises isononyl benzoate and one or more benzoic esters in a combined amount of greater than 99.9%.

19. The process according to claim 1, wherein the tin(II) catalyst is selected from the group consisting of tin(II) chloride and tin(II) sulfate.

20. The process according to claim 1, wherein the tin(II) catalyst is tin(II) benzoate.

21. The process according to claim 1, wherein the benzoate mixture is colorless.

* * * * *